(12) United States Patent
Buchholz et al.

(10) Patent No.: US 7,588,783 B2
(45) Date of Patent: Sep. 15, 2009

(54) FLAVONOID DERIVATIVE

(75) Inventors: Herwig Buchholz, Frankfurt (DE); Corinna Wirth, Darmstadt (DE); Christophe Carola, Langen (DE); Rosane Alves Fontes, Rio de Janeiro (BR)

(73) Assignee: Merck Patent GmbH, Darmstadt (DE)

( * ) Notice: Subject to any disclaimer, the term of this patent is extended or adjusted under 35 U.S.C. 154(b) by 449 days.

(21) Appl. No.: 10/581,494

(22) PCT Filed: Nov. 5, 2004

(86) PCT No.: PCT/EP2004/012538

§ 371 (c)(1), (2), (4) Date: Jun. 2, 2006

(87) PCT Pub. No.: WO2005/054222

PCT Pub. Date: Jun. 16, 2005

(65) Prior Publication Data

US 2007/0134172 A1    Jun. 14, 2007

(30) Foreign Application Priority Data

Dec. 5, 2003    (DE) ................ 103 57 004

(51) Int. Cl.
*A61K 36/00*    (2006.01)
(52) U.S. Cl. ..................................... 424/725
(58) Field of Classification Search ........................ None
See application file for complete search history.

(56) References Cited

OTHER PUBLICATIONS

Profil taxonu www..bioib.cz\cztaxon\id107366.*

* cited by examiner

*Primary Examiner*—Christopher R Tate
*Assistant Examiner*—Deborah A. Davis
(74) *Attorney, Agent, or Firm*—Millen, White, Zelano, Branigan, P.C.

(57) ABSTRACT

The invention relates to a novel flavonoid derivative, to an extract comprising the flavonoid derivative, to the cosmetic and pharmaceutical use thereof, to preparations comprising the flavonoid derivative or extract, and to a process for the preparation of the flavonoid derivative or extract.

15 Claims, No Drawings

FLAVONOID DERIVATIVE

The invention relates to a novel flavonoid derivative, to an extract comprising the flavonoid derivative, to the cosmetic and pharmaceutical use thereof, and to the use as food supplement, to preparations comprising the flavonoid derivative or extract, and to a process for the preparation of the flavonoid derivative or extract.

The human skin is subject to ageing processes, some of which are attributable to intrinsic processes (chrono-ageing) and some of which are attributable to exogenous factors (environmental, for example photo-ageing). In addition, temporary or even lasting changes to the skin picture may occur, such as, for example, acne, active or dry skin, keratoses, rosaceae, light-sensitive, inflammatory, erythematous, allergic or autoimmune-reactive reactions, such as dermatosis and photodermatosis.

The exogenous factors include, in particular, sunlight or artificial radiation sources having a comparable spectrum, and compounds which can be formed by the radiation, such as undefined reactive photoproducts, which may also be free-radical or ionic. These factors also include cigarette smoke and the reactive compounds present therein, such as ozone, free radicals, for example the hydroxyl free radical, singlet oxygen and other reactive oxygen and nitrogen compounds which interfere with the natural physiology or morphology of the skin.

The skin can be protected against exposure to light using cosmetic and/or pharmaceutical products which comprise UV filters. Particularly advantageous here are active ingredients which, besides UV protection, also have an antioxidative action and thus protect the skin both by reducing the exposure to light and also by deactivation of free radicals induced by exposure to radiation or formed in another way. Flavonoids, and in particular quercetin, have proven particularly suitable here.

However, flavonoids generally have only low water solubility and therefore can often only be incorporated into aqueous formulations in inadequate amounts. Thus, for example, quercetin has a solubility in water of only 0.04 g/l.

Skin ageing is accompanied by a reduction in the layer thicknesses of the two skin layers, the epidermis and dermis, lying one on top of the other, and it is assumed that this is at least partly responsible for the formation of wrinkles in the ageing skin. While the epidermis, the upper layer, provides the skin in particular with resistance and forms the main barrier, the dermis, the lower layer, provides the skin with strength, elasticity and thickness. The epidermis consists principally of keratinocytes, which can be divided into four different differentiation stages. The epidermal differentiation is very important for the formation of the essential skin functions, namely as protective barrier against the environment and for the prevention of water loss from the body. In the final stage of epidermal differentiation, the cornified cell envelope is formed. Under the influence of transglutaminase, crosslinking of the proteins loricrin, small proline-rich proteins and involucrin occurs. Activation of the transglutaminase is therefore also a highly promising approach for improving the skin structure and combating skin ageing (anti-ageing).

The object of the invention was to find novel compounds having valuable properties, in particular those which are suitable for use in cosmetics, pharmacy and for supplementing food.

The invention relates to a flavonoid derivative having the chemical name [5-hydroxy-7-methoxy-2-(4'-methoxyphenyl)-4-oxo-4H-chromen-8-yl]sulfonic acid monoester, and physiologically acceptable salts and solvates thereof. The compound is shown below as structural formula:

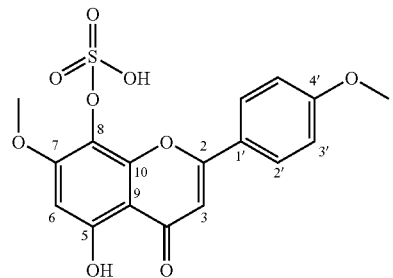

Suitable salts are all physiologically tolerated metal salts, in particular alkali metal salts, such as, for example, the sodium or potassium salt, or alkaline-earth metal salts, such as, for example, the magnesium or calcium salt, and the ammonium salt.

Solvates of [5-hydroxy-7-methoxy-2-(4'-methoxyphenyl)-4-oxo-4H-chromen-8-yl]sulfonic acid monoester are taken to mean adductions of inert solvent molecules onto [5-hydroxy-7-methoxy-2-(4'-methoxyphenyl)-4-oxo-4H-chromen-8-yl]sulfonic acid monoester which form owing to their mutual attractive force. Solvates are, for example, mono- or dihydrates or addition compounds with alcohols, such as, for example, with methanol or ethanol.

Statements regarding [5-hydroxy-7-methoxy-2-(4'-methoxyphenyl)-4-oxo-4H-chromen-8-yl]sulfonic acid monoester above and below also apply correspondingly to the physiologically acceptable salts and solvates thereof.

[5-Hydroxy-7-methoxy-2-(4'-methoxyphenyl)-4-oxo-4H-chromen-8-yl]sulfonic acid monoester absorbs ultraviolet radiation in a very broad range and at the same time has excellent water solubility (21 g/l at 25° C.). The compound is therefore particularly suitable for use as UV filter and can be incorporated in a simple manner and in a large amount into cosmetic and/or pharmaceutical preparations, foods and food supplements.

Surprisingly, [5-hydroxy-7-methoxy-2-(4'-methoxyphenyl)-4-oxo-4H-chromen-8-yl]sulfonic acid monoester also results in induction of gene expression by transglutaminase. As described above, transglutaminase plays a crucial role in the formation of a special jacket surrounding the keratinocytes, the so-called "cornified cell envelope", which is assembled in the granular layer and replaces the original membrane in the horny layer. This results in a strengthening of the skin barrier via better anchoring of the cells and thus results in an increase in the resistance of the skin to environmental influences, such as, for example, drying out.

It has furthermore been found that [5-hydroxy-7-methoxy-2-(4'-methoxyphenyl)-4-oxo-4H-chromen-8-yl]sulfonic acid monoester also induces the synthesis of the tissue inhibitor of metalloproteinase 1 precursor (TIMP1), which results in inhibition of metalloproteinase, which is held responsible, for example, for premature skin ageing in smokers. This likewise gives rise to an anti-ageing action of [5-hydroxy-7-methoxy-2-(4'-methoxyphenyl)-4-oxo-4H-chromen-8-yl]sulfonic acid monoester.

[5-Hydroxy-7-methoxy-2-(4'-methoxyphenyl)-4-oxo-4H-chromen-8-yl]sulfonic acid monoester furthermore induces the expression of the epican gene (hyaluronic acid receptor), which plays an important part in the differentiation of keratinocytes and thus results in an improvement in the skin structure. In particular, it results in formation of smooth skin.

The influence on the expression of the said genes can be detected by means of a cDNA array.

Furthermore, [5-hydroxy-7-methoxy-2-(4'-methoxyphenyl)-4-oxo-4H-chromen-8-yl]sulfonic acid monoester inhibits the arachidonic acid cascade and thus also has an antiinflammatory action.

[5-Hydroxy-7-methoxy-2-(4'-methoxyphenyl)-4-oxo-4H-chromen-8-yl]sulfonic acid monoester can advantageously be obtained by extraction from various plants. Suitable plants which contain [5-hydroxy-7-methoxy-2-(4'-methoxyphenyl)-4-oxo-4H-chromen-8-yl]sulfonic acid monoester are *Sidastrum acuminatum, Sidastrum burrerense, Sidastrum E.G. Baker, Sidastrum kicranthum, Sidastrum lodiegense, Sidastrum multiflorum, Sidastrum micranthum, Sidastrum paniculatum, Sidastrum strictum, Sidastrum tehuacanum* and *Sidastrum quinquenervium*. Particular preference is given to isolation from *Sidastrum micranthum*.

Besides [5-hydroxy-7-methoxy-2-(4'-methoxyphenyl)-4-oxo-4H-chromen-8-yl]sulfonic acid monoester itself, the extract formed on isolation thereof from plant material also has valuable properties and can be used as a pharmaceutical, cosmetic, food and/or food supplement. The invention therefore also relates to the extract comprising [5-hydroxy-7-methoxy-2-(4'-methoxyphenyl)-4-oxo-4H-chromen-8-yl] sulfonic acid monoester obtainable by extraction of plant material selected from *Sidastrum acuminatum, Sidastrum burrerense, Sidastrum E.G. Baker, Sidastrum kicranthum, Sidastrum lodiegense, Sidastrum multiflorum, Sidastrum micranthum, Sidastrum paniculatum, Sidastrum strictum, Sidastrum tehuacanum* or *Sidastrum quinquenervium*. Particular preference is given here to an extract from *Sidastrum micranthum*.

The plant extract is prepared by conventional methods of extraction of plants or plant parts. Suitable extraction methods may be: maceration, remaceration, digestion, agitation maceration, fluidised-bed extraction, ultrasound extraction, countercurrent extraction, percolation, repercolation, evacolation, diacolation or solid/liquid extraction with continuous reflux, which is carried out in a Soxhlet extractor.

All parts of the plant, preferably the above-ground parts, particularly preferably the leaves of the plant, are extracted. The solvent used for the extraction can be, for example, water or an alcohol.

The invention also relates to a process for the preparation of [5-hydroxy-7-methoxy-2-(4'-methoxyphenyl)-4-oxo-4H-chromen-8-yl]sulfonic acid monoester by extraction of plant material of the species *Sidastrum acuminatum, Sidastrum-burrerense, Sidastrum E.G. Baker, Sidastrum-kicranthum, Sidastrum lodiegense, Sidastrum multiflorum, Sidastrum micranthum, Sidastrum paniculatum, Sidastrum strictum, Sidastrum tehuacanum* or *Sidastrum quinquenervium*. The plant material used is preferably *Sidastrum micranthum*.

The way in which these extractions are carried out in detail and the crude extract obtained can be purified by generally familiar methods can be ascribed to the general knowledge of the person skilled in the art.

The extract according to the invention also encompasses plant extracts which have been subjected to further work-up after extraction in order, for example, to remove undesired accompanying substances or to increase the concentration of the desired ingredients.

The extract according to the invention can comprise [5-hydroxy-7-methoxy-2-(4'-methoxyphenyl)-4-oxo-4H-chromen-8-yl]sulfonic acid monoester in an amount of 0.1 to 100% by weight. According to a preferred embodiment, the extract comprises 5 to 100% by weight, particularly preferably 30 to 100% by weight, very particularly preferably 90 to 100% by weight, of [5-hydroxy-7-methoxy-2-(4'-methoxyphenyl)-4-oxo-4H-chromen-8-yl]sulfonic acid monoester.

Owing to the said actions and properties, [5-hydroxy-7-methoxy-2-(4'-methoxyphenyl)-4-oxo-4H-chromen-8-yl] sulfonic acid monoester and the extract comprising these compounds are highly suitable as an ingredient of preparations which can be used internally and/or externally, for example as medicaments, cosmetics, foods and/or food supplements. The invention therefore relates to preparations at least comprising [5-hydroxy-7-methoxy-2-(4'-methoxyphenyl)-4-oxo-4H-chromen-8-yl]sulfonic acid monoester and/or an extract from the above-mentioned plants and optionally excipients and/or adjuvants.

A preparation is taken to mean a formulation which comprises the active ingredient and/or the extract and is intended for use in humans or animals, for example by application to the skin, for oral ingestion, inhalation, infusion or injection. Depending on the type of preparation, the preparation may comprise excipients and/or adjuvants in addition to the active ingredient/-extract, but it may also consist exclusively of the active ingredient/extract itself, for example in the form of a powder which can be, for example, taken directly orally or inhaled. Besides the compound according to the invention or the extract according to the invention, the preparation may also comprise further active ingredients.

In the case of extraction from plant material, [5-hydroxy-7-methoxy-2-(4'-methoxyphenyl)-4-oxo-4H-chromen-8-yl] sulfonic acid monoester can be processed further either in isolated form or also in non-isolated form, i.e., for example, can be incorporated into preparations in the form of an extract or in the form of a purified extract or also in the form of the pure substance prepared from the plant extract.

The preparation preferably comprises [5-hydroxy-7-methoxy-2-(4'-methoxyphenyl)-4-oxo-4H-chromen-8-yl]sulfonic acid monoester in the form of an extract, a purified extract or in the form of the pure substance prepared from the extract.

The invention also relates to the use of [5-hydroxy-7-methoxy-2-(4'-methoxyphenyl)-4-oxo-4H-chromen-8-yl]sulfonic acid monoester or the extract for the preparation of the preparation, which is characterised in that it is a pharmaceutical preparation. It can be brought into a suitable dosage form here together with at least one solid, liquid and/or semi-liquid excipient or adjuvant and optionally in combination with one or more further active ingredients.

According to a preferred embodiment, the preparation according to the invention is characterised in that it is a medicament.

The medicaments can be used in human or veterinary medicine. Suitable excipients are organic or inorganic substances which are suitable for enteral (for example oral), parenteral or topical administration and do not react with [5-hydroxy-7-methoxy-2-(4'-methoxyphenyl)-4-oxo-4H-chromen-8-yl]sulfonic acid monoester or the extract, for example water, vegetable oils, benzyl alcohols, alkylene glycols, polyethylene glycols, glycerol triacetate, gelatine, carbohydrates, such as lactose or starch, magnesium stearate, talc or Vaseline. Suitable for oral use are, in particular, tablets, pills, dragees, capsules, powders, granules, syrups, juices or drops, suitable for rectal use are suppositories, suitable for parenteral use are solutions, preferably oily or aqueous solutions, furthermore suspensions, emulsions or implants, and suitable for topical use are ointments, creams or powders. The plant extracts may also be lyophilised and the resultant lyophilisates used, for example, for the preparation of injection preparations. The preparations indicated may be sterilised and/or comprise adjuvants, such as lubricants, preservatives, stabilisers and/or wetting agents, emulsifiers, salts for modifying the osmotic pressure, buffer substances, dyes, flavours and/or a plurality of further active ingredients, for example one or more vitamins.

[5-Hydroxy-7-methoxy-2-(4'-methoxyphenyl)-4-oxo-4H-chromen-8-yl]sulfonic acid monoester or the extract is generally preferably administered in doses of between about 1 and 500 mg, in particular between 5 and 100 mg, per dosage unit. The daily dose is preferably between about 0.02 and 10 mg/kg of body weight. However, the specific dose for each patient depends on a very wide variety of factors, for example on the efficacy of the specific compound employed, on the age, body weight, general state of health, sex, on the diet, on the time and method of administration, on the excretion rate, medicament combination and severity of the particular disease to which the therapy applies.

The pharmaceutical formulations comprising one or more plant extract(s) can be prepared with the aid of techniques which are well known to the person skilled in the art.

According to a further preferred embodiment, the preparation is characterised in that it is a cosmetic composition.

Particular preference is given to a preparation which is characterised in that it is a skin-treatment composition.

A skin-treatment composition is a cosmetic, dermatological or pharmaceutical preparation which is suitable for topical use. The preparation typically comprises conventional skin-tolerated excipients which have been tested in accordance with the application and optionally further adjuvants and active ingredients.

The present application therefore furthermore relates to a preparation for topical use comprising
 a) [5-hydroxy-7-methoxy-2-(4'-methoxyphenyl)-4-oxo-4H-chromen-8-yl]sulfonic acid monoester and/or an extract, as described above,
 b) a skin-tolerated excipient, and
 c) optionally one or more further active ingredients having a skin-care and/or inflammation-inhibiting action.

Owing, inter alia, to the above-mentioned UV absorption by [5-hydroxy-7-methoxy-2-(4'-methoxyphenyl)-4-oxo-4H-chromen-8-yl]sulfonic acid monoester, a preparation comprising this compound and/or the extract is also suitable for the protection of human skin or for the protection of body cells against oxidative stress, i.e., for example, against damage by free radicals, as are produced by sunlight. The protection against ultraviolet radiation by the preparation according to the invention can be further augmented by incorporation of one or more further UV filters.

The invention therefore also relates to a preparation which is characterised in that it furthermore comprises one or more UV filters.

In principle, all UV filters are suitable for a combination. Particular preference is given to UV filters whose physiological acceptability has already been demonstrated. Both for UV-A and UV-B filters, there are many proven substances known from the specialist literature, for example benzylidenecamphor derivatives, such as
 3-(4'-methylbenzylidene)-dl-camphor (for example Eusolex® 6300),
 3-benzylidenecamphor (for example Mexoryl® SD),
 polymers of N-{(2 and 4)-[(2-oxoborn-3-ylidene)methyl]benzyl}acryl-amide (for example Mexoryl® SW),
 N,N,N-trimethyl-4-(2-oxoborn-3-ylidenemethyl)anilinium methylsulfate (for example Mexoryl® SK) or
 α-(2-oxoborn-3-ylidene)toluene-4-sulfonic acid (for example Mexoryl® SL), benzoyl- or dibenzoylmethanes, such as
 1-(4-tert-butylphenyl)-3-(4-methoxyphenyl)propane-1,3-dione (for example Eusolex® 9020) or
 4-isopropyldibenzoylmethane (for example Eusolex® 8020), benzophenones, such as
 2-hydroxy-4-methoxybenzophenone (for example Eusolex® 4360) or
 2-hydroxy-4-methoxybenzophenone-5-sulfonic acid and its sodium salt (for example Uvinul® MS-40), methoxycinnamic acid esters, such as
 octyl methoxycinnamate (for example Eusolex® 2292) or
 isopentyl 4-methoxycinnamate, for example as a mixture of the isomers (for example Neo Heliopan® E 1000), salicylate derivatives, such as
 2-ethylhexyl salicylate (for example Eusolex® OS),
 4-isopropylbenzyl salicylate (for example Megasol®) or
 3,3,5-trimethylcyclohexyl salicylate (for example Eusolex® HMS), 4-aminobenzoic acid and derivatives, such as
 4-aminobenzoic acid,
 2-ethylhexyl 4-(dimethylamino)benzoate (for example Eusolex® 6007) or
 ethoxylated ethyl 4-aminobenzoate (for example Uvinul® P25), benzimidazole derivatives, such as
 2-phenylbenzimidazole-5-sulfonic acid and potassium, sodium and triethanolamine salts thereof (for example Eusolex® 232),
 2,2'-(1,4-phenylene)bis(1H-benzimidazole-4,6-disulfonic acid, mono-sodium salt) (CAS No. 180 898-37-7),
 2,2'-(1,4-phenylene)bis(1H-benzimidazol-5-sulfonic acid) and potassium, sodium and triethanolamine salts thereof, and further substances, such as
 2-ethylhexyl 2-cyano-3,3-diphenylacrylate (for example Eusolex® OCR),
 3,3'-(1,4-phenylenedimethylene)bis(7,7-dimethyl-2-oxo-bicyclo[2.2.1]-hept-1-ylmethanesulfonic acid and salts thereof (for example Mexoryl® SX),
 2,4,6-trianilino-(p-carbo-2'-ethylhexyl-1 '-oxy)-1,3,5-triazine (for example Uvinul®T 150),
 2-(2H-benzotriazol-2-yl)-4-methyl-6-(2-methyl-3-(1,3,3,3-tetramethyl-1-(trimethylsilyloxy)disiloxanyl)propyl)phenol (for example Silatrizole®),
 2-ethylhexyl 4,4'-[(6-[4-((1,1-dimethylethyl)aminocarbonyl)phenyl-amino]-1,3,5-triazine-2,4-diyl)diimino]bis(benzoate) (for example Uvasorb® HEB),
 α-(trimethylsilyl)-ω-[trimethylsilyl)oxy]poly[oxy[dimethyl [and about 6% of methyl[2-[p-[2,2-bis(ethoxycarbonyl]vinyl]phenoxy]-1-methyleneethyl] and approximately 1.5% of methyl[3-[p-[2,2-bis(ethoxycarbonyl)vinyl)-phenoxy)propenyl) and 0.1 to 0.4% of (methylhydrogen]silylene]] (n≈60) (CAS No. 207 574-74-1),
 2,2'-methylenebis(6-(2H-benzotriazol-2-yl)-4-(1,1,3,3-tetramethylbutyl)-phenol) (CAS No. 103 597-45-1),
 2,4-bis{[4-(2-ethylhexyloxy)-2-hydroxy]phenyl}-6-(4-methoxyphenyl)-1,3,5-triazine (CAS No. 103 597-45-, 187 393-00-6).

The compounds mentioned in the list should only be regarded as examples. It is of course also possible to use other UV filters. These organic UV filters are generally incorporated into the preparations according to the invention, in particular into cosmetic formulations, in an amount of 0.5 to 20% by weight, preferably in an amount of 1 to 15% by weight and particularly preferably in amounts of 2 to 8% by weight, per individual substance. If, besides [5-hydroxy-7-methoxy-2-(4'-methoxyphenyl)-4-oxo-4H-chromen-8-yl] sulfonic acid monoester and/or the extract according to the invention, the preparation according to the invention comprises further organic UV filters, these are usually present in an amount of up to 40% by weight, preferably in an amount of 5 to 25% by weight, based on the total weight of the formulation, in particular in the case of cosmetic formulations.

Conceivable inorganic UV filters are those from the group of the titanium dioxides, such as, for example, coated titanium dioxide (for example Eusolex® T-2000, Eusolex® T-AQUA), zinc oxides (for example Sachtotec®), iron oxides or also cerium oxides. These inorganic UV filters are generally present in an amount of 0.5 to 20% by weight, preferably in an amount of 2 to 10% by weight, based on the total weight of the formulation, in particular in the case of cosmetic formulations.

If different inorganic or organic UV filters are employed, these can be used in virtually any desired ratios to one another. The ratios of the individual substances to one another are usually in the range 1:10-10:1, preferably in the range 1:5-5:1 and particularly preferably in the range 1:2-2:1. If UV-A and UV-B filters are employed, it is advantageous for most applications for the proportion of UV-B filters to predominate and the ratio of UV-A filters:UV-B filters to be in the range 1:1 to 1:10.

Preferred compounds having UV-filtering properties which may preferably be present in the preparation according to the invention, in particular if this is a cosmetic preparation, are 3-(4'-methylbenzylidene)-dl-camphor, 1-(4-tert-butylphenyl)-3-(4-methoxyphenyl)propane-1,3-dione, 4-isopropyidi-benzoylmethane, 2-hydroxy-4-methoxybenzophenone, octyl methoxy-cinnamate, 3,3,5-trimethylcyclohexyl salicylate, 2-ethylhexyl 4-(dimethyl-amino)benzoate, 2-ethylhexyl 2-cyano-3,3-diphenylacrylate.

As described above, [5-hydroxy-7-methoxy-2-(4'-methoxyphenyl)-4-oxo-4H-chromen-8-yl]sulfonic acid monoester and the extract comprising this compound have, inter alia, the following actions: they increase the resistance of the skin to environmental influences, such as, for example, drying out, counter skin ageing, result in an improvement in the skin structure, in particular in the formation of smooth skin, and have an antiinflammatory action. The invention therefore also relates to the use of [5-hydroxy-7-methoxy-2-(4'-methoxyphenyl)-4-oxo-4H-chromen-8-yl]sulfonic acid monoester and/or the extract comprising this compound for the preparation of a pharmaceutical and/or cosmetic preparation for increasing the resistance of the skin to environmental influences, in particular drying out, for preventing skin ageing, for improving the skin structure, in particular for the formation of smooth skin.

[5-Hydroxy-7-methoxy-2-(4'-methoxyphenyl)-4-oxo-4H-chromen-8-yl]sulfonic acid monoester and the extract comprising this compound also act as free-radical scavengers and thus counter oxidative stress. They furthermore have an antiallergic and anti-irritative action and can thus be used for the treatment or preventative treatment of allergies, inflammation and irritation, in particular of the skin. The invention therefore also relates to the use of [5-hydroxy-7-methoxy-2-(4'-methoxyphenyl)-4-oxo-4H-chromen-8-yl]sulfonic acid monoester and/or the extract comprising this compound for the preparation of a pharmaceutical and/or cosmetic preparation for protection against oxidative stress and for combating allergies, inflammation and irritation. Preference is given to preparations for topical use on the skin.

In order that [5-hydroxy-7-methoxy-2-(4'-methoxyphenyl)-4-oxo-4H-chromen-8-yl]sulfonic acid monoester and the extract comprising this compound are able to develop their positive action as free-radical scavengers on the skin particularly well, it may be advantageous to allow them to penetrate into deeper skin layers. If the penetration depth into epidermal layers is inadequate, this can be increased by means of suitable transport agents, for example liposomes, which facilitate transport of the compound through the outer skin layers. Finally, systemic transport of [5-hydroxy-7-methoxy-2-(4'-methoxyphenyl)-4-oxo4H-chromen-8-yl] sulfonic acid monoester is also conceivable. The preparation is then designed, for example, in such a way that it is suitable for oral administration.

As already mentioned, [5-hydroxy-7-methoxy-2-(4'-methoxyphenyl)-4-oxo-4H-chromen-8-yl]sulfonic acid monoester and the extract comprising this compound act as free-radical scavengers. Free radicals of this type are not only produced by sunlight, but are also formed under various conditions. Examples are anoxia, which blocks the flow of electrons upstream of the cytochrome oxidases and causes the formation of superoxide free-radical anions; inflammation associated, inter alia, with the formation of superoxide anions by the membrane NADPH oxidase of the leukocytes, but also associated with the formation (through disproportionation in the presence of iron(II) ions) of the hydroxyl free radicals and other reactive species which are normally involved in the phenomenon of phagocytosis; and lipid autoxidation, which is generally initiated by a hydroxyl free radical and produces lipidic alkoxy free radicals and hydroperoxides.

Owing to their actions, [5-hydroxy-7-methoxy-2-(4'-methoxyphenyl)-4-oxo-4H-chromen-8-yl]sulfonic acid monoester and the extract comprising this compound are also suitable for the preparation of preparations for immune protection and for the protection of DNA and RNA. In particular, the preparations obtained are suitable for the protection of DNA and RNA against oxidative attacks, against free radicals and against damage by radiation, in particular UV radiation. If the compound/extract is used in the form of preparations for use on the skin, a double protective action against UV radiation arises: through absorption of UV radiation, which prevents it acting on the skin, and through the action as free-radical scavenger, which counters the free radicals induced by UV radiation nevertheless penetrating.

Furthermore, [5-hydroxy-7-methoxy-2-(4'-methoxyphenyl)-4-oxo-4H-chromen-8-yl]sulfonic acid monoester and the extract comprising this compound are suitable for the preparation of preparations for cell protection, in particular for the protection of Langerhans cells against damage by the above-mentioned influences. The present invention therefore expressly also relates to the use of a preparation comprising [5-hydroxy-7-methoxy-2-(4'-methoxyphenyl)-4-oxo4H-chromen-8-yl]sulfonic acid monoester and/or the extract comprising this compound for the said purposes.

The preparation according to the invention is also suitable for the treatment of skin diseases associated with a keratinisation disorder which affects differentiation and cell proliferation, in particular for the treatment of acne vulgaris, acne comedonica, polymorphic acne, acne rosaceae, nodular acne, acne conglobata, age-induced acne, acne which arises as a side effect, such as acne solaris, medicament-induced acne or acne professionalis, for the treatment of other keratinisation disorders, in particular ichthyosis, ichthyosiform states, Darier's disease, keratosis palmoplantaris, leukoplasia, leukoplasiform states, herpes of the skin and mucous membrane (buccal) (lichen), for the treatment of other skin diseases associated with a keratinisation disorder and which have an inflammatory and/or immunoallergic component and in particular all forms of psoriasis which affect the skin, mucous membranes and fingers and toenails, and psoriatic rheumatism and skin atopy, such as eczema or respiratory atopy, or hypertrophy of the gums, it furthermore being possible for the compounds to be used for some inflammation which is not associated with a keratinisation disorder, for the treatment of all benign or malignant excrescence of the dermis or epidermis, which may be of viral origin, such as verruca vulgaris, verruca plana, epidermodysplasia verruciformis, oral papillomatosis, papillomatosis florida, and excrescence which may be caused by UV radiation, in particular epithelioma baso-cellulare and epithelioma spinocellulare, for the treatment of other skin diseases, such as dermatitis bullosa and diseases affecting the collagen, for the treatment of certain eye diseases, in particular corneal diseases, for overcoming or combating light-induced skin ageing associated with ageing, for reducing pigmentation and keratosis actinica and for the treatment of all diseases associated with normal ageing or light-induced ageing, for the prevention or healing of wounds/scars of atrophy of the epidermis and/or dermis caused by locally or systemically used corticosteroids and all other types of skin atrophy, for the prevention or treatment of defects in wound healing, for the prevention or elimination of stretch marks caused by pregnancy or for the promotion of wound healing, for combating defects in sebum production, such as hyper-seborrhoea in acne or simple seborrhoea, for combating or preventing cancer-like states or pre-carcinogenic states, in particular promyelocytic leukaemia, for the treatment of inflammatory diseases, such as arthritis, for the treatment of all virus-induced diseases of the skin or other areas of the body, for the prevention or treatment of alopecia, for the treatment of skin diseases or diseases of other areas of the body with an immunological component, for the treatment of cardiovascular diseases, such as arteriosclerosis or hypertension, and of non-insulin-dependent diabetes, and for the treatment of skin problems caused by UV radiation.

The protective action against oxidative stress or against the effect of free radicals can be further improved if the preparation according to the invention comprises one or more further antioxidants. The invention therefore furthermore relates to a preparation which is characterised in that it comprises one or more further antioxidant(s).

There are many proven substances known from the specialist literature which may be present as antioxidants, for example amino acids (for example glycine, histidine, tyrosine, tryptophan) and derivatives thereof, imidazoles (for example urocanic acid) and derivatives thereof, peptides, such as D,L-carnosine, D-carnosine, L-carnosine and derivatives thereof (for example anserine), carotinoids, carotenes (for example α-carotene, β-carotene, lycopene) and derivatives thereof, chlorogenic acid and derivatives thereof, lipoic acid and derivatives thereof (for example dihydrolipoic acid), aurothioglucose, propylthiouracil and other thiols (for example thioredoxin, glutathione, cysteine, cystine, cystamine and the glycosyl, N-acetyl, methyl, ethyl, propyl, amyl, butyl and lauryl, palmitoyl, oleyl, ∩-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts), and sulfoximine compounds (for example buthionine sulfoximines, homocysteine sulfoximine, buthionine sulfones, penta-, hexa- and heptathionine sulfoximine) in very low tolerated doses (for example pmol to μmol/kg), and also (metal) chelating agents (for example α-hydroxy fatty acids, palmitic acid, phytic acid, lactoferrin), α-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof, vitamin C and derivatives (for example ascorbyl palmitate, magnesium ascorbyl phosphate, ascorbyl acetate), tocopherols and derivatives (for example vitamin E acetate), vitamin A and derivatives (for example vitamin A palmitate), and coniferyl benzoate of benzoin resin, rutinic acid and derivatives thereof, α-glycosyl rutin, ferulic acid, furfurylideneglucitol, carnosine, butylhydroxytoluene, butylhydroxy-anisole, nordihydroguaiaretic acid, trihydroxybutyrophenone, quercetin, uric acid and derivatives thereof, mannose and derivatives thereof, zinc and derivatives thereof (for example ZnO, $ZnSO_4$), selenium and derivatives thereof (for example selenomethionine), stilbenes and derivatives thereof (for example stilbene oxide, trans-stilbene oxide).

Mixtures of antioxidants are likewise suitable for use in the preparation according to the invention. Known and commercial mixtures are, for example, mixtures comprising, as active ingredients, lecithin, L-(+)-ascorbyl palmitate and citric acid (for example Oxynex® AP), natural tocopherols, L-(+)-ascorbyl palmitate, L-(+)-ascorbic acid and citric acid (for example Oxynex® K LIQUID), tocopherol extracts from natural sources, L-(+)-ascorbyl palmitate, L-(+)-ascorbic acid and citric acid (for example Oxynex® L LIQUID), DL-α-tocopherol, L-(+)-ascorbyl palmitate, citric acid and lecithin (for example Oxynex® LM) or butylhydroxytoluene (BHT), L-(+)-ascorbyl palmitate and citric acid (for example Oxynex® 2004).

The preparation according to the invention preferably comprises, as further antioxidant(s), one or more flavonoids and/or coumaranones, by means of which the protection thereof against UV radiation and/or oxidative stress is considerably improved. The invention therefore also relates to a preparation which is characterised in that it comprises one or more further compound(s) selected from the group of the flavonoids and/or coumaranones.

Flavonoids are taken to mean the glycosides of flavonones, flavones, 3-hydroxyflavones (=flavonols), aurones, isoflavones and rotenoids [Römpp Chemie Lexikon [Römpp's Lexicon of Chemistry], Volume 9, 1993]. For the purposes of the present invention, however, this term is also taken to mean the aglycones, i.e. the sugar-free constituents, and the derivatives of the flavonoids and aglycones. For the purposes of the present invention, the term flavonoid is furthermore also taken to mean anthocyanidine (cyanidine). For the purposes of the present invention, the term coumaranones is also taken to mean derivatives thereof.

Preferred flavonoids are derived from flavonones, flavones, 3-hydroxy-flavones, aurones and isoflavones, in particular from flavonones, flavones, 3-hydroxyflavones and aurones.

The flavonoids are preferably selected from the following compounds: 4,6,3',4'-tetrahydroxyaurone, quercetin, rutin, isoquercetin, eriodictyol, taxifolin, luteolin, trihydroxyethylquercetin (troxequercetin), trishydroxyethylrutin (troxerutin), trishydroxyethylisoquercetin (troxeisoquercetin), trishydroxyethylluteolin (troxeluteolin) and sulfates and phosphates thereof.

Of the flavonoids, particular preference is given to rutin and troxerutin. Very especial preference is given to troxerutin.

Of the coumaranones, preference is given to 4,6,3',4'-tetrahydroxybenzyl-3-coumaranone.

The proportion of the one or more antioxidants in the preparations according to the invention, in particular in the cosmetic formulation, is preferably from 0.001 to 5% by weight, particularly preferably from 0.01 to 2% by weight, based on the formulation as a whole.

The preparation according to the invention may comprise vitamins as further ingredients. The cosmetic formulations according to the invention preferably comprise vitamins and vitamin derivatives selected from vitamin A, vitamin A propionate, vitamin A palmitate, vitamin A acetate, retinol, vitamin B, thiamine chloride hydrochloride (vitamin $B_1$), riboflavin (vitamin $B_2$), nicotinamide, vitamin C (ascorbic acid), vitamin D, ergocalciferol (vitamin $D_2$), vitamin E, DL-α-tocopherol, tocopherol E acetate, tocopherol hydrogensuccinate, vitamin $K_1$, esculin (vitamin P active ingredient), thiamine (vitamin $B_1$), nicotinic acid (niacin), pyridoxine, pyridoxal, pyridoxamine (vitamin $B_6$), pantothenic acid, biotin, folic acid and cobalamine (vitamin $B_{12}$), particularly preferably vitamin A palmitate, vitamin C, DL-α-tocopherol, tocopherol E acetate, nicotinic acid, pantothenic acid and biotin.

The preparation according to the invention, in particular the cosmetic or pharmaceutical formulation, may furthermore also comprise ectoine [(S)-1,4,5,6-tetrahydro-2-methyl-4-pyrimidinecarboxylic acid] as ingredient and then effects protection of skin cells, in particular protection of the Langerhans cells.

The inflammation-inhibiting action described above of the preparation according to the invention comprising [5-hydroxy-7-methoxy-2-(4'-methoxy-phenyl)-4-oxo-4H-chromen-8-yl]sulfonic acid monoester and/or an extract comprising this compound can be further improved if one or more 1-(2-hydroxyaryl)alkan-1-one oximes (as described, for example, in EP 0 149 242), preferably 2-hydroxy-5-methyl-laurophenone oxime, is/are furthermore present. Particularly advantageous are formulations comprising [5-hydroxy-7-methoxy-2-(4'-methoxyphenyl)-4-oxo-4H-chromen-8-yl]-sulfonic acid monoester and/or an extract comprising this compound and 2-hydroxy-5-methyllaurophenone oxime, in which the said substances are present in a weight ratio of 1:10 to 10:1. Use forms of such formulations are, for example, after-sun preparations.

Further active ingredients can also be incorporated into the preparation according to the invention, in particular the cosmetic and/or pharmaceutical formulation, for example hydroxyectoine [(S,S)-1,4,5,6-tetrahydro-5-hydroxy-2-methyl-4-pyrimidinecarboxylic acid]

active ingredients which can serve for wound treatment, such as, for example, allantoin insect repellents, such as, for example, ethyl 3-[N-n-butyl-N-acetyl]-aminopropionate [CAS No. 52304-36-6]

sorbitol for skin care [for example Karion®F liquid or Karion®FP liquid]

biotin anti-ageing products, such as, for example, mixtures comprising hydroxyproline or derivatives of hydroxyproline, for example mixtures comprising lecithin, hydroxyproline dipalmitate, sitosterol, linoleic acid, tocopherol, sodium ascorbate, mannitol, phenoxyethanol, methylparaben, ethylparaben, propylparaben, butylparaben, water [for example RonaCare™ ASC III®] or, for example, mixtures comprising lecithin, hydroxylated lecithin, L-hydroxyproline, disodium rutinyl disulfate, phenoxyethanol, mannitol, magnesium ascorbyl phosphate, methylparaben, ethylparaben, propylparaben, butylparaben, sitosterol, tocopherol, sodium ascorbate, water [for example RonaCare™ VTA]

bisabolol.

[5-Hydroxy-7-methoxy-2-(4'-methoxyphenyl)-4-oxo-4H-chromen-8-yl]sulfonic acid monoester and the extract comprising this compound can be incorporated into the preparation according to the invention in a conventional manner. Preference is given to formulations for external use, for example as a cream, lotion, gel, or as a solution which can be sprayed onto the skin. It is preferred here for the preparation to comprise at least one oil phase and at least one water phase.

Use forms of the preparations according to the invention which may be mentioned are, for example: solutions, emulsions, PIT emulsions, suspensions, pastes, ointments, gels, creams, soaps, surfactant-containing cleansing preparations, lotions, oils, powders, sprays and aerosols. Further use forms are, for example, sticks, shampoos and shower products. In addition to [5-hydroxy-7-methoxy-2-(4'-methoxyphenyl)-4-oxo-4H-chromen-8-yl]sulfonic acid monoester and/or the extract comprising this compound, any desired conventional excipients, adjuvants and optionally further active ingredients may be added to the formulation.

Preferred adjuvants originate from the group of the preservatives, antioxidants, stabilisers, solubilisers, vitamins, colorants, odour improvers, film formers, thickeners and humectants.

Solutions and emulsions can comprise the conventional excipients, such as solvents, solubilisers and emulsifiers, for example water, ethanol, isopropanol, ethyl carbonate, ethyl acetate, benzyl alcohol, benzyl benzoate, propylene glycol, 1,3-butyl glycol, oils, in particular cottonseed oil, ground-nut oil, maize-germ oil, olive oil, castor oil and sesame oil, glycerol fatty acid esters, polyethylene glycols and fatty acid esters of sorbitan, or mixtures of these substances.

The emulsions can exist in various forms. Thus, they can be, for example, an emulsion or microemulsion of the water-in-oil (W/O) type, or of the oil-in-water (O/W) type, or a multiple emulsion, for example of the water-in-oil-in-water (W/O/W) type.

The preparation may also be in the form of an emulsifier-free, disperse formulation. It can be, for example, a hydrodispersion or a Pickering emulsion.

The preparation may also be in the form of a PIT emulsion or hydrogel and may also comprise liposomes, which encompass, for example, active ingredients.

Suspensions can comprise the conventional excipients, such as liquid diluents, for example water, ethanol or propylene glycol, suspension media, for example ethoxylated isostearyl alcohols, polyoxyethylene sorbitol esters and polyoxyethylene sorbitan esters, microcrystalline cellulose, aluminium metahydroxide, bentonite, agar-agar and tragacanth, or mixtures of these substances.

Pastes, ointments, gels and creams can comprise the conventional excipients, for example animal and vegetable fats, waxes, paraffins, starch, tragacanth, cellulose derivatives, polyethylene glycols, silicones, bentonites, silicic acid, talc and zinc oxide, or mixtures of these substances.

Soaps can comprise the conventional excipients, such as alkali metal salts of fatty acids, salts of fatty acid monoesters, fatty acid protein hydrolysates, isethionates, lanolin, fatty alcohol, vegetable oils, plant extracts, glycerol, sugars, or mixtures of these substances.

Surfactant-containing cleansing products can comprise the conventional excipients, such as salts of fatty alcohol sulfates, fatty alcohol ether sulfates, sulfosuccinic acid monoesters, fatty acid protein hydrolysates, isethionates, imidazolinium derivatives, methyl taurates, sarcosinates, fatty acid amide ether sulfates, alkylamidobetaines, fatty alcohols, fatty acid glycerides, fatty acid diethanolamides, vegetable and synthetic oils, lanolin derivatives, ethoxylated glycerol fatty acid esters, or mixtures of these substances.

Face and body oils can comprise the conventional excipients, such as synthetic oils, such as fatty acid esters, fatty alcohols, silicone oils, natural oils, such as vegetable oils and oily plant extracts, paraffin oils, lanolin oils, or mixtures of these substances.

Powders and sprays can comprise the conventional excipients, for example milk sugar, talc, silicic acid, aluminium hydroxide, calcium silicate and polyamide powder, or mixtures of these substances. Sprays can additionally comprise the conventional propellants, for example chlorofluorocarbons, propane/butane or dimethyl ether.

Further use forms of the preparation according to the invention are also lipsticks, lip-care sticks, mascara, eyeliner, eyeshadow, rouge, powder, emulsion and wax make-up, and sunscreen, pre-sun and after-sun preparations.

All compounds or components which can be used in the preparation according to the invention are either known and commercially available or can be synthesised by known processes.

The formulation can comprise adjuvants which are usually used in preparations of this type, such as, for example, thickeners, plasticisers, humectants, surface-active agents, emulsifiers, preservatives, antifoaming agents, perfumes, waxes, lanolin, propellants, dyes and/or pigments which colour the agent itself or the skin, and other ingredients usually used in cosmetics.

The dispersant or solubiliser used can be an oil, wax or other fatty body, a lower monoalcohol or a lower polyol, or mixtures thereof. The particularly preferred monoalcohols or polyols include ethanol, i-propanol, propylene glycol, glycerol and sorbitol.

A preferred embodiment of the invention is an emulsion which is in the form of a protective cream or milk and, in addition to [5-hydroxy-7-methoxy-2-(4'-methoxyphenyl)-4-oxo-4H-chromen-8-yl]sulfonic acid monoester and/or an extract comprising this compound and optionally further light-protection filters, comprises fatty alcohols, fatty acids, fatty acid esters, in particular triglycerides of fatty acids, lanolin, natural or synthetic oils or waxes and emulsifiers in the presence of water.

Further preferred embodiments are oily lotions based on natural or synthetic oils and waxes, lanolin, fatty acid esters, in particular triglycerides of fatty acids, or oily/alcoholic lotions based on a lower alcohol, such as ethanol, or a glycol, such as propylene glycol, and/or a polyol, such as glycerol, and oils, waxes and fatty acid esters, such as triglycerides of fatty acids.

The preparation according to the invention can also be in the form of an alcoholic gel which comprises one or more lower alcohols or polyols, such as ethanol, propylene glycol or glycerol, and a thickener, such as siliceous earth. The oily/alcoholic gels additionally comprise natural or synthetic oil or wax.

The solid sticks consist of natural or synthetic waxes and oils, fatty alcohols, fatty acids, fatty acid esters, lanolin and other fatty bodies.

If a preparation is formulated as an aerosol, the conventional propellants, such as alkanes, fluoroalkanes and chlorofluoroalkanes, are generally used.

The formulation may also be used to protect the hair against photochemical damage in order to prevent colour changes, bleaching or damage of a mechanical nature. A suitable formulation here is in the form of a rinse-out shampoo, lotion, gel or emulsion, the formulation in question being applied before or after shampooing, before or after colouring or bleaching or before or after permanent waving. It is also possible to select a formulation in the form of a lotion or gel for styling and treating the hair, in the form of a lotion or gel for brushing or laying a water wave, in the form of a hair lacquer, permanent-waving composition, colorant or bleach for the hair. In addition to [5-hydroxy-7-methoxy-2-(4'-methoxyphenyl)-4-oxo-4H-chromen-8-yl]sulfonic acid monoester and/or an extract comprising this compound and further UV filters, the formulation may comprise various adjuvants used in this type of composition, such as surface-active agents, thickeners, polymers, softeners, preservatives, foam stabilisers, electrolytes, organic solvents, silicone derivatives, oils, waxes, antigrease agents, dyes and/or pigments which colour the composition itself or the hair, or other ingredients usually used for hair care.

The preparation according to the invention can be prepared with the aid of techniques which are well known to the person skilled in the art.

For the protection of the skin and/or natural or sensitised hair against sunlight, a cosmetic preparation comprising [5-hydroxy-7-methoxy-2-(4'-methoxyphenyl)-4-oxo-4H-chromen-8-yl]sulfonic acid monoester and/or an extract comprising this compound is applied to the skin or the hair. Sensitised hair here is taken to mean hair which has been subjected to chemical treatment, such as permanent-wave treatment, or a colouring or bleaching process.

Furthermore, [5-hydroxy-7-methoxy-2-(4'-methoxyphenyl)-4-oxo-4H-chromen-8-yl]sulfonic acid monoester and/or the extract comprising this compound also have a stabilising action on the formulation. On use in corresponding products, these therefore also remain stable for longer and do not change their appearance. In particular, the efficacy of the ingredients, for example vitamins, is retained even on extended use or extended storage. This is particularly advantageous in the case of compositions for the protection of the hair against the action of UV rays, since these cosmetics are subjected to particularly high stresses by the UV radiation.

The advantageous properties of [5-hydroxy-7-methoxy-2-(4'-methoxy-phenyl)-4-oxo-4H-chromen-8-yl]sulfonic acid monoester or the extract comprising this compound can also be utilised, for example, in their use in foods or as food supplements or as "functional food". For example, [5-hydroxy-7-methoxy-2-(4'-methoxyphenyl)-4-oxo-4H-chromen-8-yl]sulfonic acid monoester and/or the extract comprising this compound can furthermore protect the compounds present in the food, the food supplement or the functional food and also the organism against oxidation or against the action of free radicals.

The invention therefore also relates to a food which is enriched with [5-hydroxy-7-methoxy-2-(4'-methoxyphenyl)-4-oxo-4H-chromen-8-yl]sulfonic acid monoester and/or an extract comprising this compound.

The invention furthermore relates to a food supplement which comprises [5-hydroxy-7-methoxy-2-(4'-methoxyphenyl)-4-oxo-4H-chromen-8-yl]sulfonic acid monoester and/or an extract comprising this compound. Food supplements are preferably preparations in the sense of the general definition given above and are preferably administered orally.

The further explanations given for foods also apply correspondingly to food supplements and functional food. The foods which can be enriched in accordance with the present invention with [5-hydroxy-7-methoxy-2-(4'-methoxyphenyl)-4-oxo-4H-chromen-8-yl]sulfonic acid monoester and/or an extract comprising this compound encompass all materials which are suitable for consumption by animals or for consumption by humans, for example vitamins and provitamins thereof, fats, minerals or amino acids. Foods which can be enriched in accordance with the present invention with [5-hydroxy-7-methoxy-2-(4'-methoxyphenyl)-4-oxo-4H-chromen-8-yl]sulfonic acid monoester and/or an extract comprising this compound are, for example, also foods which originate from a single natural source, such as, for example, sugar, unsweetened juice, squash or puree of a single plant species, such as, for example, unsweetened apple juice (for example also a mixture of different types of apple juice), grapefruit juice, orange juice, apple compote, apricot squash, tomato juice, tomato sauce, tomato puree, etc. Further examples of foods which can be enriched in accordance with the present invention [5-hydroxy-7-methoxy-2-(4'-methoxyphenyl)-4-oxo-4H-chromen-8-yl]sulfonic acid monoester and/or an extract comprising this compound are corn or cereals from a single plant species and materials produced from plant species of this type, such as, for example, cereal syrup, rye flour, wheat flour or oat bran. Mixtures of foods of this type are also suitable for being enriched in accordance with the present invention with [5-hydroxy-7-methoxy-2-(4'-methoxyphenyl)-4-oxo-4H-chromen-8-yl]-sulfonic acid monoester and/or an extract comprising this compound, for example multivitamin preparations, mineral mixtures or sweetened juice. As further examples of foods which can be enriched in accordance with the present invention with [5-hydroxy-7-methoxy-2-(4'-methoxyphenyl)-4-oxo-4H-chromen-8-yl]sulfonic acid monoester and/or an extract comprising this compound, mention may be made of food preparations, for example prepared cereals, biscuits, mixed drinks, foods prepared especially for children, such as yoghurt, diet foods, low-calorie foods or animal feeds.

The foods which can be enriched in accordance with the present invention with [5-hydroxy-7-methoxy-2-(4'-methoxyphenyl)-4-oxo-4H-chromen-8-yl]-sulfonic acid monoester and/or an extract comprising this compound thus include all edible combinations of carbohydrates, lipids, proteins, inorganic elements, trace elements, vitamins, water and active metabolites of plants and animals.

The foods which can be enriched in accordance with the present invention with [5-hydroxy-7-methoxy-2-(4'-methoxyphenyl)-4-oxo-4H-chromen-8-yl]-sulfonic acid monoester and/or an extract comprising this compound and food supplements comprising [5-hydroxy-7-methoxy-2-(4'-methoxyphenyl)-4-oxo-4H-chromen-8-yl]sulfonic acid monoester and/or an extract comprising this compound are preferably administered orally, for example in the form of meals, pills, tablets, capsules, powders, syrups, solutions or suspensions.

As described, valuable cosmetic preparations, pharmaceutical preparations, foods and/or food supplements can be prepared by use/incorporation of [5-hydroxy-7-methoxy-2-(4'-methoxyphenyl)-4-oxo-4H-chromen-8-yl]sulfonic acid monoester and/or the extract comprising this compound in/into pharmaceutical and/or cosmetic preparations, foods and/or food supplements. The invention therefore also expressly relates to the use of [5-hydroxy-7-methoxy-2-(4'-methoxyphenyl)-4-oxo-4H-chromen-8-yl]sulfonic acid monoester and/or an extract comprising this compound for the preparation of a cosmetic preparation, a pharmaceutical preparation, a food and/or a food supplement.

If the preparation according to the invention comprises [5-hydroxy-7-methoxy-2-(4'-methoxyphenyl)-4-oxo-4H-chromen-8-yl]sulfonic acid monoester as pure substance, this compound is present in the following amounts, based on the preparation as a whole:

in the case where the preparation is a cosmetic and/or pharmaceutical formulation, in an amount of 0.001 to 100% by weight, preferably in an amount of 0.01 to 30% by weight, particularly preferably in an amount of 0.1 to 10% by weight in the case where the preparation is a food, in an amount of 0.00001 to 20% by weight, preferably in an amount of 0.001 to 10% by weight, and in the case where the preparation is a food supplement, preferably 0.1 to 80% by weight, based on the food supplement as a whole.

If the preparation according to the invention comprises an extract comprising [5-hydroxy-7-methoxy-2-(4'-methoxyphenyl)-4-oxo-4H-chromen-8-yl]-sulfonic acid monoester, this is present in the following amounts, based on the preparation as a whole:

in the case where the preparation is a cosmetic and/or pharmaceutical formulation, in an amount of 0.01 to 100% by weight, preferably in an amount of 0.1 to 60% by weight, particularly preferably in an amount of 1 to 30% by weight in the case where the preparation is a food, in an amount of 0.01 to 20% by weight, preferably in an amount of 0.1 to 10% by weight, and in the case where the preparation is a food supplement, preferably 0.1 to 80% by weight, based on the food supplement as a whole.

The foods enriched with [5-hydroxy-7-methoxy-2-(4'-methoxyphenyl)-4-oxo-4H-chromen-8-yl]sulfonic acid monoester and/or an extract comprising this compound can be prepared with the aid of techniques which are well known to the person skilled in the art.

Even without further comments, it is assumed that a person skilled in the art will be able to utilise the above description in the broadest scope. The preferred embodiments should therefore merely be regarded as descriptive disclosure which is absolutely not limiting in any way.

The complete disclosure content of all applications and publications mentioned above and below is incorporated into this application by way of reference.

All compounds or components which can be used in the preparations according to the invention are either known and commercially available or can be synthesised by known methods.

The INCI names of the raw materials used are as follows (the INCI names are by definition given in English):

| Raw material | INCI name |
| --- | --- |
| Abil WE 09 | Polyglyceryl-4-Isostearate, Cetyl Dimethicone Copolyol, Hexyl Laurate |
| Antaron V-220 | PVP/Eicosene Copolymer |
| Arlacel 80 | Sorbitan Oleate |
| Arlacel 165 V | Glyceryl Stearate, PEG-100 Stearate |
| Avocado oil | Persea Gratissima |
| Beeswax | Beeswax |
| Biobase ™ EP | Glyceryl Stearate, Cetearyl Alcohol, Sodium Stearoyl Lactylate, Lecithin |
| Carbopol ETD 2050 | Carbomer |
| Cetiol V | Decyl Oleate |
| Cetyl alcohol | Cetyl Alcohol |
| Cetyl isononanoate | Cetyl Isononanoate |
| Cutina HR | Hydrogenated Castor Oil |
| Dimethicone | Dimethicone |
| Eusolex ® 232 | Phenylbenzimidazole Sulfonic Acid |
| Eusolex ® 2292 | Octyl Methoxycinnamate, BHT |
| Eusolex ® 6300 | 4-Methylbenzylidene Camphor |
| Eusolex 8300 | 4-Methylbenzylidene |
| Eusolex ® 9020 | Butyl Methoxydibenzoylmethane |

-continued

| Raw material | INCI name |
| --- | --- |
| Eusolex ® HMS | Homosalate |
| Eusolex T-Aqua | Aqua (Water), Titanium Dioxide, Alumina, Sodium Metaphosphate, Phenoxyethanol, Sodium Methylparaben |
| Eutanol G | Octyldodecanol |
| Germaben II | Propylene Glycol, Diazolidinyl Urea, Methylparaben, Propylparaben |
| Germaben II-E | Propylene Glycol, Diazolidinyl Urea, Methylparaben, Propylparaben |
| Glycerin | Glycerin |
| Glycerin (87%) | Glycerin |
| Glycerin (87% extra pure) | Glycerin |
| Glycerin, anhydrous | Glycerin |
| Hetester PHA | Propylene Glycol Isoceteth-3 Acetate |
| Hexyl laurate | Hexyl Laurate |
| Imwitor 960 K flakes | Glyceryl Stearate SE |
| Isolan PDI | Diisostearoyl Polyglyceryl-3-Diisostearat |
| Isopropyl myristate | Isopropyl Myristate |
| Isopropyl palmitate | Isopropyl Palmitate |
| Jojoba oil | Buxus Quinensis (Jojoba Oil) |
| Karion F liquid | Sorbitol |
| Keltrol RD | Xanthan Gum |
| Magnesium sulfate | Magnesium Sulfate |
| Magnesium sulfate heptahydrate | Magnesium Sulfate |
| Methyl 4-hydroxybenzoate | Methylparaben |
| Miglyol 812 | Caprylic/Capric Triglyceride |
| Miglyol 812 N | Caprylic/Capric Triglyceride |
| Miglyol 812, neutral oil | Caprylic/Capric Triglyceride |
| Mirasil CM5 | Cyclomethicone |
| Mirasil DM 350 | Dimethicone |
| Montanov 68 | Cetearyl Alcohol, Cetearyl Glucoside |
| Oxynex ® K | PEG-8, Tocopherol, Ascorbyl Palmitate, Ascorbic Acid, Citric Acid |
| Panthenol-D | Panthenol |
| Paracera M | Microwax |
| Paraffin oil, liquid | Mineral Oil |
| Perfume oil TND-2417 | Parfum |
| Pemulen TR-1 | Acrylates/$C_{10-30}$ Alkyl Acrylate Crosspolymer |
| Pemulen ® TR-2 | Acrylates/$C_{10-30}$ Alkyl Acrylate Crosspolymer |
| Performa ® V 825 | Synthetic Wax |
| Polyglyceryl 2-dipolyhydroxystearate | Polyglyceryl-2 Dipolyhydroxystearate |
| Prisorine 2021 | Isopropyl Isostearate |
| Propane-1,2-diol | Propylene Glycol |
| Propyl 4-hydroxybenzoate | Propylparaben |
| Rhodicare S | Xanthan Gum |
| RonaCare ™ ASC III | Aqua, Lecithin, Dipalmitoyl Hydroxyproline, Phenoxyethanol, Tall Oil Sterol, Linoleic Acid, Tocopherol, Sodium Ascorbate, Mannitol, Methylparaben, Ethylparaben, Propylparaben, Butylparaben |
| RonaCare ™ bisabolol | Bisabolol |
| RonaCare ™ ectoine | Ectoine |
| RonaCare ™ LPO | Lauryl p-Cresol Ketoxime |
| RonaCare ™ tocopherol acetate | Tocopheryl Acetate |
| Sepigel 305 | Polyacrylamide, $C_{13-14}$ Isoparaffin, Laureth-7 |
| SFE 839 | Cyclopentasiloxane, Dimethicone/Vinyldimethicone Crosspolymer |
| Shea butter | Shea Butter |
| Steareth-2 | Steareth-2 |
| Steareth-10 | Steareth-10 |
| Stearic acid | Stearic Acid |
| Sodium chloride | Sodium Chloride |
| Sodium hydroxide solution, 10% | Sodium Hydroxide |
| DL-α-tocopherol acetate | Tocopherol Acetate |
| Triethanolamine | Triethanolamine |
| Triethanolamine extra pure | Triethanolamine |
| Water, demineralised | Aqua (Water) |
| Zinc stearate | Zinc Stearate |

The examples explain the invention without being restricted thereto.

EXAMPLE 1

Detection of the Antiinflammatory Activity

The antiinflammatory properties of [5-hydroxy-7-methoxy-2-(4'-methoxy-phenyl)-4-oxo-4H-chromen-8-yl]sulfonic acid monoester can be demonstrated in the keratinocyte monolayer $PGE_2$ model. In order to induce inflammation, keratinocytes are incubated with the pro-inflammatory substance phorbol myristate acetate (PMA) for 24 hours in 96-well plates (15,000 cells/well). The preincubated cells (final concentration of PMA 0.1 μg/ml) are incubated with $10^{-6}$ M indometacin (positive control) or 0.2 mM [5-hydroxy-7-methoxy-2-(4'-methoxyphenyl)-4-oxo-4H-chromen-8-yl]sulfonic acid monoester for 24 hours. The negative control used is a control culture comprising no PMA. After incubation, the content of prostaglandin $E_2$ ($PGE_2$) in all three samples is determined by ELISA kits.

EXAMPLE 2

Extraction 10 kg of leaf material from *Sidastrum micranthum* are extracted twice with 120 liters of hot ethanol. The combined extracts are concentrated to 10 litres, stirred for 2 hours at below 10° C. with 5 kg of ice and 5 liters of cold water, and filtered. The filtrate (20 litres) is concentrated to 8 liters while heating under reduced pressure.

After cooling to below 25° C., the mixture is filtered. The filtrate obtained is concentrated further to a total solids content of 10% and filtered at 35° C. in order to remove the accompanying flavonoid. The filtrate obtained is concentrated further to a total solids content of 20% and filtered at 35° C. The resultant cake comprising [5-hydroxy-7-methoxy-2-(4'-methoxyphenyl)-4-oxo-4H-chromen-8-yl]sulfonic acid monoester is washed with 70% ethanol. The filtrate is concentrated to a solids content of 45% in order to increase the yield. When room temperature is reached, the mixture is filtered, and the cake comprising [5-hydroxy-7-methoxy-2-(4'-methoxyphenyl)-4-oxo-4H-chromen-8-yl]sulfonic acid monoester is likewise washed with 70% ethanol, giving [5-hydroxy-7-methoxy-2-(4'-methoxyphenyl)-4-oxo-4H-chromen-8-yl]sulfonic acid monoester in a yield of 1.2% by weight, based on the dried leaves.

$^{13}$C NMR data:

δ [ppm] (in DMSO): 55.43 (O$\underline{C}$H$_3$), 56.38 (O$\underline{C}$H$_3$), 95.90 (C-6), 102.70 (C-3); 103.69 (C-9), 114.27 (C-5',C-3'),122.58 (C-8), 123.00 (C-1'), 129.06 (C-2', C-6'), 149.33 (C-10), 156.93 (C-5), 159.02 (C-7), 162.29 (C-4'), 163.92 (C-2), 182.13 ($\underline{C}$=O)

$^1$H NMR data:

δ [ppm], 3.90 (s, 3H, C$\underline{H}_3$) 3.95 (s, 3H, C$\underline{H}_3$) 6.55 (s,1 H, H-6), 6.85 (s, 1H, H-3), 7.1 (d, 2H, H-5', H-3'), 8.1 (d, 2H, H-2',H6'), 12.9 (s, 1H, OH).

Mass spectrum
Maldi/MS: 824.9 (2M+K), 392.9 (M–H)⁻, 152.9

Assays

Expression of the Transglutaminase Gene

The culture medium in cell cultures (human keratinocytes) is replaced by culture medium with (test) or without test substance (control). The cells are cultivated further for a defined time, harvested and frozen at –80°.

The RNA is extracted, where each culture comprises about 200 μg of RNA. The solution is adjusted to 1 μg/μl of RNA and treated with DNAse I in order to remove all DNA residues. The amount of RNA is adjusted to 2 μg/ml.

The mRNA is transcribed to cDNA $^{32}$P-labelled samples and purified by chromatography.

The DNA sequences are immobilised on cDNA chip membranes and hybridised (overnight at 68° C). The membranes are washed intensively, and the radioactivity of each measurement point is measured. An increase in the radioactivity means upregulation of the corresponding RNA compared with the control.

Determination of Transglutaminase by PCR (Polymerase Chain Reaction)

Human keratinocytes are incubated with the test substance, and the RNA is extracted with Tri-Reagent. The RNA of the transglutaminase is transcribed with biotinylated oligo(dT) and Superscript II reverse transcriptase. The measurement is carried out using a LightCycler (Roche), with the fluorescence being measured continuously during the PCR cycles. The ratio of "fluorescence" and the number of PCR cycles gives the relative expression of transglutaminase RNA.

Transglutaminase Enzyme Activity in Cell Cultures

Human keratinocytes are cultivated. A sample is incubated with 50 μM test substance and cultivated for 96 hours. The positive control used is 1.5 mM CaCl$_2$, and the negative control used is 1 μM retinol. An untreated sample serves as control. TGk is extracted from the cells. The enzyme activity is measured by covalent bonding of $^3$H-putrescine to casein. Casein is precipitated using trichloroacetic acid and measured by liquid scintillation after purification and drying.

EXAMPLE 3

| | Lotion (W/O) for application to the skin | |
|---|---|---|
| | | % by wt. |
| A | Polyglyceryl 2-dipolyhydroxystearate | 5.0 |
| | Beeswax | 0.5 |
| | Zinc stearate | 0.5 |
| | Hexyl laurate | 9.0 |
| | Cetyl isononanoate | 6.0 |
| | Shea butter | 0.5 |
| | DL-α-tocopherol acetate | 1.0 |
| | [5-hydroxy-7-methoxy-2-(4'-methoxyphenyl)-4-oxo-4H-chromen-6-yl]sulfonic acid monoester | 0.5 |
| B | Glycerin | 5.0 |
| | Magnesium sulfate heptahydrate | 1.0 |
| | Preservatives | q.s. |
| | Water, demineralised | to 100 |

Preparation

Phase A is warmed to 75° C. and phase B to 80° C. Phase B is slowly added to phase A with stirring. After homogenisation, the mixture is cooled with stirring. Perfumes are added at a temperature of 40° C.

The following are used as preservatives:
0.05% of propyl 4-hydroxybenzoate
0.15% of methyl 4-hydroxybenzoate

EXAMPLE 4

| | Lotion (W/O) for application to the skin | |
|---|---|---|
| | | % by wt. |
| A | Polyglyceryl 2-dipolyhydroxystearate | 5.0 |
| | Beeswax | 0.5 |
| | Zinc stearate | 0.5 |
| | Hexyl laurate | 9.0 |
| | Cetyl isononanoate | 6.0 |
| | Shea butter | 0.5 |
| | DL-α-tocopherol acetate | 1.0 |
| B | [5-Hydroxy-7-methoxy-2-(4'-methoxyphenyl)-4-oxo-4H-chromen-6-yl]sulfonic acid monoester | 1.0 |
| | Glycerin | 5.0 |
| | Magnesium sulfate heptahydrate | 1.0 |
| | Preservatives | q.s. |
| | Water, demineralised | to 100 |

Preparation

Phase A is warmed to 75° C. and phase B to 80° C. Phase B is slowly added to phase A with stirring. After homogenisation, the mixture is cooled with stirring. Perfumes are added at a temperature of 40° C.

The following are used as preservatives:
0.05% of propyl 4-hydroxybenzoate
0.15% of methyl 4-hydroxybenzoate

EXAMPLE 5

| | Lotion (W/O) for application to the skin | |
|---|---|---|
| | | % by wt. |
| A | 4,6,3',4'-Tetrahydroxybenzylcoumaranone-3 | 1.0 |
| | Polyglyceryl 2-dipolyhydroxystearate | 5.0 |
| | Beeswax | 0.5 |
| | Zinc stearate | 0.5 |
| | Hexyl laurate | 9.0 |
| | Cetyl isononanoate | 6.0 |
| | Shea butter | 0.5 |
| | DL-α-tocopherol acetate | 1.0 |
| | [5-Hydroxy-7-methoxy-2-(4'-methoxyphenyl)-4-oxo-4H-chromen-6-yl]sulfonic acid monoester | 1.0 |
| B | Glycerin | 5.0 |
| | Magnesium sulfate heptahydrate | 1.0 |
| | Preservatives | q.s. |
| | Water, demineralised | to 100 |

Preparation

Phase A is warmed to 75° C. and phase B to 80° C. Phase B is slowly added to phase A with stirring. After homogenisation, the mixture is cooled with stirring. Perfumes are added at a temperature of 40° C.

The following are used as preservatives:
0.05% of propyl 4-hydroxybenzoate
0.15% of methyl 4-hydroxybenzoate

EXAMPLE 6

A cream (O/W) comprising ectoine is prepared from the following components:

| | | % by wt. |
|---|---|---|
| A | Paraffin, low viscosity (1) | 8.0 |
| | Isopropyl myristate (1) | 4.0 |
| | Mirasil CM5 (2) | 3.0 |
| | Stearic acid (1) | 3.0 |
| | Arlacel 165 V (3) | 5.0 |
| | [5-Hydroxy-7-methoxy-2-(4'-methoxyphenyl)-4-oxo-H-chromen-6-yl]sulfonic acid monoester | 1.0 |
| B | Glycerin (87%) (1) | 3.0 |
| | Germaben II (4) | 0.5 |
| | Water, demineralised | to 100 |
| C | RonaCare ™ ectoine (1) | 1.0 |

Preparation

Firstly, phases A and B are warmed separately to 75° C. Phase A is then slowly added to phase B with stirring, and stirring is continued until a homogeneous mixture is formed. After homogenisation of the emulsion, the mixture is cooled to 30° C. with stirring. The mixture is subsequently warmed to 35° C., phase C is added, and the mixture is stirred to homogeneity.

Sources of Supply
(1) Merck KGaA
(2) Rhodia
(3) Uniqema
(4) ISP

EXAMPLE 7

| | Topical composition as W/O emulsion | |
|---|---|---|
| | | % by wt. |
| A | Isolan PDI (2) | 3.0 |
| | Paraffin oil, liquid (1) | 17.0 |
| | Isopropyl myristate | 5.0 |
| | Beeswax | 0.2 |
| | Cutina HR (2) | 0.3 |
| | [5-Hydroxy-7-methoxy-2-(4'-methoxyphenyl)-4-oxo-H-chromen-6-yl]sulfonic acid monoester | 1.0 |
| B | Water, demineralised | to 100 |
| | Glycerin (87%) | 4.0 |
| | Magnesium sulfate | 1.0 |
| | Germaben II-E (3) | 1.0 |
| C | RonaCare ™ LPO (1) | 2.0 |

Preparation

Phases A and B are warmed to 75° C. Phase B is added to phase A with stirring. The mixture is subsequently homogenised using the Turrax at 9000 rpm for 2 min. The resultant mixture is cooled to 30 to 35° C., and C is stirred in.

Sources of Supply
(1) Merck KGaA
(2) Goldschmidt AG
(3) ISP

The invention claimed is:

1. The compound [5-Hydroxy-7-methoxy-2-(4'-methoxyphenyl)-4-oxo-4H-chromen-8-yl]sulfonic acid monoester, or a physiologically acceptable salt or solvate thereof, in substantially isolated form.

2. A composition comprising the substantially isolated compound according to claim 1 and optionally excipients and/or adjuvants.

3. A composition according to claim 2, in a medicament form.

4. A composition according to claim 2, in a cosmetic composition form.

5. A composition according to claim 3, in a skin-treatment composition form.

6. A composition in a form for topical use comprising:
   a) the substantially isolated compound according to claim 1,
   b) a skin-tolerated excipient, and
   c) optionally one or more further active ingredients having a skin-care and/or inflammation-inhibiting action.

7. A composition according to claim 5, which furthermore comprises one or more UV filters.

8. A composition according to claim 2, which comprises one or more further antioxidant(s).

9. A composition according to claim 2, which comprises one or more further compound(s) selected from the group of the flavonoids and/or coumaranones.

10. A food which is enriched with the substantially isolated compound according to claim 1.

11. A food supplement which comprises the substantially isolated compound according to claim 1.

12. A process for the preparation of the compound according to claim 1 which comprises extracting from plant material of the species *Sidastrum acuminatum, Sidastrum-bufferense, Sidastrum E.G. Baker, Sidastrum-kicranthum, Sidastrum lodiegense, Sidastrum multiflorum, Sidastrum micranthum, Sidastrum paniculatum, Sidastrum strictum, Sidastrum tehuacanum* or *Sidastrum quinquenervium*, to provide an extract and obtaining the compound in substantially isolated form therefrom.

13. Process according to claim 12, characterised in that the plant material used is *Sidastrum micranthum*.

14. A method for preparing a cosmetic composition, a pharmaceutical composition, a food and/or a food supplement which comprises combining a compound according to claim 1 with at least one excipient suitable for a cosmetic, at least one excipient suitable for a pharmaceutical, at least one food or at least one excipient suitable for a food supplement.

15. A method for increasing the resistance of the skin to environmental influences, for increasing resistance of the skin to drying out, for treating skin ageing, for improving the skin structure, and/or for improving the formation of smooth skin which comprises topically apply to the skin a composition comprising the substantially isolated compound of claim 1.

* * * * *

UNITED STATES PATENT AND TRADEMARK OFFICE
CERTIFICATE OF CORRECTION

PATENT NO. : 7,588,783 B2
APPLICATION NO. : 10/581494
DATED : September 15, 2009
INVENTOR(S) : Buchholz et al.

It is certified that error appears in the above-identified patent and that said Letters Patent is hereby corrected as shown below:

Column 22, line 35 reads "of the species *Sidastrum acuminatum, Sidastrum-bufferense*," should read --of the species *Sidastrum acuminatum, Sidastrum-burrerense*,--

Signed and Sealed this

First Day of December, 2009

David J. Kappos
*Director of the United States Patent and Trademark Office*

UNITED STATES PATENT AND TRADEMARK OFFICE
CERTIFICATE OF CORRECTION

PATENT NO. : 7,588,783 B2  Page 1 of 1
APPLICATION NO. : 10/581494
DATED : September 15, 2009
INVENTOR(S) : Buchholz et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 551 days.

Signed and Sealed this

Twenty-first Day of September, 2010

David J. Kappos
*Director of the United States Patent and Trademark Office*